US009448166B1

(12) United States Patent
Rainer

(10) Patent No.: US 9,448,166 B1
(45) Date of Patent: Sep. 20, 2016

(54) METHODS AND APPARATUS FOR THE MEASUREMENT OF MALT BEVERAGES

(71) Applicant: Michael D. Rainer, Burton, OH (US)

(72) Inventor: Michael D. Rainer, Burton, OH (US)

(73) Assignee: The Mercury Iron and Steel Co., Solon, OH (US)

( * ) Notice: Subject to any disclaimer, the term of this patent is extended or adjusted under 35 U.S.C. 154(b) by 0 days.

(21) Appl. No.: 14/676,483

(22) Filed: Apr. 1, 2015

Related U.S. Application Data

(60) Provisional application No. 61/975,450, filed on Apr. 4, 2014.

(51) Int. Cl.
*G01N 21/41* (2006.01)

(52) U.S. Cl.
CPC ..... *G01N 21/4133* (2013.01); *G01N 2021/414* (2013.01); *G01N 2201/0621* (2013.01); *G01N 2201/0633* (2013.01)

(58) Field of Classification Search
CPC .. G01N 21/43; G01N 21/4133; G01N 21/55; G01N 21/552; G01N 21/553; C12C 7/01; C12C 5/00; C12C 1/00
USPC ................................................ 356/128–137
See application file for complete search history.

(56) References Cited

U.S. PATENT DOCUMENTS

| 4,433,913 | A  | * | 2/1984  | Harmer ................ G01N 21/431 250/227.11 |
| 5,355,211 | A  | * | 10/1994 | Thompson ............. G01N 21/43 356/135 |
| 6,374,845 | B1 | * | 4/2002  | Melendez .............. G01N 21/43 137/3 |
| 6,707,542 | B1 | * | 3/2004  | Cotton ............... G01N 21/4133 356/136 |
| 7,268,864 | B2 | * | 9/2007  | Chiarello ........... G01N 21/0303 356/128 |
| 2006/0240147 | A1 | * | 10/2006 | Padhye ..................... C12C 5/00 426/16 |
| 2010/0085560 | A1 | * | 4/2010  | Fedele .................... A47J 31/00 356/134 |
| 2010/0260889 | A1 | * | 10/2010 | Elvig ..................... C12C 7/047 426/12 |

* cited by examiner

*Primary Examiner* — Hoa Pham
(74) *Attorney, Agent, or Firm* — Ulmer & Berne LLP

(57) ABSTRACT

A method is provided for determining a physical property of a malt beverage sample. The method includes measuring a refractive index of the malt beverage sample. The method further includes determining a temperature-compensated measured refractive index by temperature correcting the measured refractive index relative to a predetermined reference temperature. The temperature correcting is specific to the total dissolved solids of the malt beverage sample. The method also includes converting the temperature-compensated measured refractive index to a unit of measurement. The unit of measurement relates to a physical property of the malt beverage sample. Apparatus are also provided.

20 Claims, 7 Drawing Sheets

FIG 3.

| | 30 | 31 | 32 | 33 | 34 | 35 | 36 | 37 | 38 |
|---|---|---|---|---|---|---|---|---|---|
| | WORT Sample ID | A. Paar DMA5000 MEASURED D20/20 | TEST UNIT MEASURED D20/20 | TEST UNIT ERROR D20/20 | A. Paar DMA5000 MEASURED OE (°P) | ATAGO WM-7 MEASURED Brix % | ATAGO WM-7 ERROR Brix % | TEST UNIT MEASURED %DS | TEST UNIT ERROR %DS |
| | G | 1.033 | 1.033 | 0.000 | 8.2 | 8.4 | -0.2 | 8.2 | 0.0 |
| | B | 1.034 | 1.033 | 0.001 | 8.4 | 8.6 | -0.2 | 8.4 | 0.0 |
| | E | 1.034 | 1.034 | 0.000 | 8.5 | 8.7 | -0.2 | 8.4 | 0.1 |
| | D | 1.034 | 1.034 | 0.000 | 8.5 | 8.7 | -0.2 | 8.4 | 0.1 |
| | A | 1.035 | 1.035 | 0.000 | 8.7 | 8.9 | -0.2 | 8.6 | 0.1 |
| | H | 1.035 | 1.035 | 0.000 | 8.7 | 9.0 | -0.3 | 8.7 | 0.0 |
| | C | 1.035 | 1.035 | 0.000 | 8.8 | 9.1 | -0.3 | 8.7 | 0.1 |
| | F | 1.035 | 1.035 | 0.000 | 8.8 | 9.1 | -0.3 | 8.7 | 0.1 |
| | L | 1.037 | 1.037 | 0.000 | 9.2 | 9.6 | -0.4 | 9.2 | 0.0 |
| | K | 1.048 | 1.049 | -0.001 | 12.0 | 12.6 | -0.7 | 12.1 | -0.2 |
| | J | 1.075 | 1.076 | -0.001 | 18.2 | 18.8 | -0.6 | 18.2 | 0.0 |
| | I | 1.079 | 1.080 | -0.001 | 19.1 | 19.7 | -0.6 | 19.1 | -0.1 |

METHODS AND APPARATUS FOR THE MEASUREMENT OF MALT BEVERAGES

REFERENCE TO RELATED APPLICATION

This application claims priority of U.S. provisional patent application Ser. No. 61/975,450, filed Apr. 4, 2014, and hereby incorporates this provisional patent application by reference herein in its entirety.

TECHNICAL FIELD

Methods and apparatus are provided for measuring one or more physical properties of interest with respect to the production beer or other malt beverages.

BACKGROUND

Malt beverages, including beer, date back some 7,000 years and are among the oldest beverage products in the world.

SUMMARY

In accordance with a first embodiment, a method is disclosed for determining one or more physical properties of a malt beverage. The method includes measuring a refractive index of a malt beverage sample, temperature correcting the measured refractive index relative to a predetermined reference temperature, converting the temperature-compensated measured refractive index to a given unit of measure which is related to one or more physical properties of interest, and outputting the one or more physical properties of interest.

In accordance with a second embodiment, an apparatus comprises an optical measurement system. The optical measurement system comprises a light source, a fluid measurement surface, optical elements, a light sensing means, a temperature measuring means, a processing means, and an output means. The apparatus is configured so that a portion of light energy from the light source is directed through one or more of the optical elements until the light energy is incident upon and optically coupled with a fluid sample in contact with the fluid measuring surface. Whereupon the light energy is reflected toward and measured by the light sensing means. A first signal from the light sensing means is processed by the processing means in such a manner as to convert the first signal from the light sensing means into refractive index units. The processing means also converts a second signal from a temperature measuring means into usable units of temperature. Using the units of temperature, the processing means corrects the refractive index units to correspond with a predetermined reference temperature specific to the fluid under test. The processing means continues to further process the corrected refractive index units by converting it into one or more units of measure related to physical properties of the fluid sample. Once the physical properties of the fluid sample have been determined, those units are then output using the output means.

In accordance with a third embodiment, the apparatus of the second embodiment further comprises a memory storage means and a user input means. The apparatus is configured to store and recall from the memory storage means the results of past measurement. Inputs entered by a user using the user input means are stored in the memory storage means. The processor uses at least one of the results of past measurement and the inputs to calculate or determine other information requested by the user.

In accordance with a fourth embodiment, an apparatus comprises an optical measurement system. The optical measurement system comprises a measuring surface, one or more optical elements, a reticle, and a magnifying means. The apparatus is configured so that light energy incident at a grazing angle to the measuring surface is transmitted through a fluid sample and through the measuring surface. The optical element(s) then focus a shadowline, created by a critical angle of the fluid sample, onto the reticle. A scale is etched or otherwise inscribed onto a surface of the reticle. The position of the shadowline relative to divisions of the scale is directly related to one or more physical properties of the fluid sample. The magnifying means enlarges the scale and shadowline on the reticle to make it human readable.

In accordance with a fifth embodiment, a method is disclosed wherein an apparatus uses a predetermined physical relationship between refractive index and malt beverage properties, together with predetermined refractive index temperature corrections, to determine and output certain physical properties of a malt beverage.

In accordance with a sixth embodiment, the apparatus of the fifth embodiment is configured to measure Brix units and convert those units using a correction factor that has been predetermined or entered by a user.

In accordance with a seventh embodiment, an apparatus comprises an optical measurement system. The optical measurement system comprises a light source, a fluid measurement surface, optical elements, a light sensor, a temperature sensor, a processor, and an output device. The apparatus is configured so that a portion of light energy from the light source is directed through one or more of the optical elements until the light energy is incident upon and optically coupled with a fluid sample in contact with the fluid measuring surface. Whereupon, the light energy is reflected toward and measured by the light sensor. A first signal from the light sensor is processed by the processor in such a manner as to convert the first signal from the light sensor into refractive index units. The processor also converts a second signal from a temperature sensor into units of temperature. Using the units of temperature, the processor corrects the refractive index units to correspond with a predetermined reference temperature specific to the fluid under test. The processor continues to further process the corrected refractive index units by converting it into one or more units of measure related to physical properties of the fluid sample. Once the physical properties of the fluid sample have been determined, those units are then output using the output device.

In accordance with an eighth embodiment, the apparatus of the seventh embodiment further comprises a memory storage device and a user input device. The apparatus is configured to store and recall from the memory storage device the results of past measurement. Inputs entered by a user using the user input device are stored in the memory storage device. The processor uses at least one of the results of past measurement and the inputs to calculate or determine other information requested by the user.

In accordance with a ninth embodiment, an apparatus comprises an optical measurement system. The optical measurement system comprises a measuring surface, one or more optical elements, a reticle, and a magnifying device. The apparatus is configured so that light energy incident at a grazing angle to the measuring surface is transmitted through a fluid sample and through the measuring surface. The optical element(s) then focus a shadowline, created by a critical angle of the fluid sample, onto the reticle. A scale is etched or otherwise inscribed onto a surface of the reticle. The position of the shadowline relative to divisions of the scale is directly related to one or more physical properties of the fluid sample. The magnifying device enlarges the scale and shadowline on the reticle to make it human readable.

In accordance with a tenth embodiment, a method is provided for determining a physical property of a malt beverage sample. The method comprises measuring a refractive index of the malt beverage sample. The method further comprises determining a temperature-compensated measured refractive index by temperature correcting the measured refractive index relative to a predetermined reference temperature. The temperature correcting is specific to the total dissolved solids content of the malt beverage sample. The method also comprises converting the temperature-compensated measured refractive index to a different unit of measurement. The new unit of measurement relates to a physical property of the malt beverage sample.

In accordance with an eleventh embodiment, an apparatus is configured for determining a physical property of a malt beverage sample. The apparatus comprises a refractive index sensor, a temperature sensor, and a processor. The processor is configured to receive a first signal from the refractive index sensor and a second signal from the temperature sensor. The processor is configured to convert the first signal to a refractive index measurement. The processor is further configured to determine a correction factor in response to the second signal. The correction factor is specific to the total dissolved solids of a malt beverage sample. The processor is further configured to apply the correction factor to the refractive index measurement to obtain a temperature-compensated refractive index measurement. The processor is additionally configured to convert the temperature-compensated refractive index measurement into a unit of measurement relating to a physical property of a malt beverage sample.

BRIEF DESCRIPTION OF THE DRAWINGS

It is believed that certain embodiments will be better understood from the following description taken in conjunction with the accompanying drawings in which:

FIG. 3 shows results of independent laboratory testing on the disclosed methods and apparatus.

DETAILED DESCRIPTION

Figure 1:
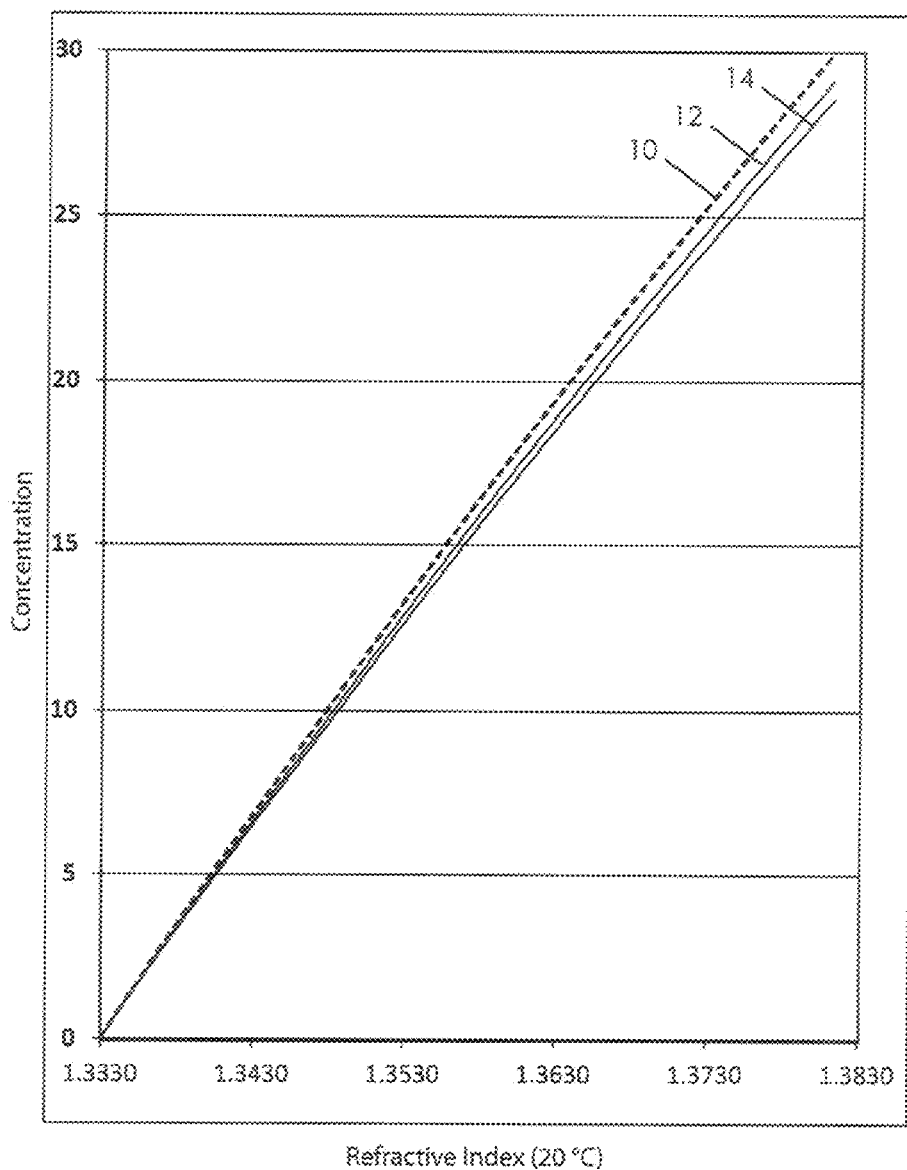
FIG. 1 is a graph comparing refractive index to sucrose concentration, dissolved solids of wort, and the approximated refractometer correction factor for wort sugars.

Malt beverages, including beer, date back some 7,000 years and are among the oldest beverage products in the world. From its humble beginnings as an industry, necessity warranted the creation of various standards and methods for measurement. The need for standards in commercial brewing is driven by commercial requirements for accurately measuring the extract content of the wort for determination of excise taxes. Most of these methods initially relied on the hydrometer, or some other primitive measure related to specific gravity, to provide an indication of sugar or alcohol concentration. However, refractometers have now proven themselves to be useful tools for the brewer.

In the US and Canada, beer is primarily taxed based on the volume removed from the brewery. In Europe, however, taxation is country dependent and is either based on the ° Plato per hectoliters (strength of original extract by volume) or, in some cases, the alcohol content per hectoliter.

Primarily, measurement is about quality control. For instance, even though beer in the US is taxed based on its volume, it is still industry best practice for the beer chemist or brewer to keep accurate records of beer measurements.

The brewing process often involves various steps include malting, mashing, lautering, boiling, and fermenting. In the begin stages, starches in the grains are processed and turned to malt. They are then milled to help release sugars during mashing. As the grains go through mashing, enzymes are released, the starches are converted to sugars, and mash becomes wort. The wort is then strained and boiled with hops, after which it is then quickly cooled, the yeast is added, and fermentation begins.

It is important for the beer maker to know the sugar content of the wort. Wort sugars consist of a complex blend of carbohydrates including mostly maltose with dextrins, monosaccharides, maltotriose, and a small amount of sucrose, with the remainder consisting of larger saccharides, and other material which is non-fermentable by standard brewer's yeast (in general, saccharides larger than DP3). In some examples, only about five to six percent of wort sugars are sucrose.

The most direct method of wort measurement consists of measuring its specific gravity with a hydrometer, a method that has been used for hundreds of years. In the mid-19$^{th}$ and early 20$^{th}$ centuries, Brix, Plato, and Balling each independently empirically determined the relationship between specific gravity and the percent by weight of sucrose in sucrose water mixtures. Equations and conversion formulas exist for converting specific gravity into a unit of measure named after each of these inventors. These units have been used for measuring wort for more than 100 years.

Hydrometers can be problematic for measuring wort. For instance, hydrometers require a fairly substantial sample of wort in which to float. Furthermore, since specific gravity is very temperature dependent, hydrometer scales are only valid at one particular temperature. Hence, they must be used in conjunction with a thermometer, and any variation from the hydrometer's reference temperature must be noted and compensated.

Various types of refractometers (e.g., handheld, inline, and benchtop) have been used with limited success for the best part of the last hundred years. A refractometer is an optical instrument designed to measure the concentration or mixture ratio of water soluble fluids. It measures refractive index, the speed at which light passes through a liquid. The denser the liquid, the slower the light will travel through it, and the higher its reading will be on the refractometer. Like hydrometers, many different scales are available that convert refractive index into a unit of measure that is more meaningful, i.e., Brix, specific gravity, ° Plato, etc.

Refractometers designed for field use are usually rugged and portable. An advantage over the hydrometer is the relatively small sample size that is required for testing. This also saves time required for cleaning and sanitizing the hydrometer equipment. Although refractometers are also dependent on temperature, certain refractometers are made with a temperature compensating arrangement.

Refractometers used in the brewing process are usually equipped with a Brix scale. Brix represents the physical/mathematical relationship between refractive index and the content of sucrose per weight in a sucrose water solution. However, since there is very little sucrose in beer wort, there is typically an error between Brix readings and the true dissolved solids or sugar content of wort. Brix readings on a refractometer tend to overestimate the true concentration of sugars by 1.02 to 1.05 times. As a result, when using a Brix refractometer with brewing software or online calculators, it is common to enter a correction factor to compensate for this error.

Providing that the Brix refractometer is equipped with a method of temperature correction or compensation, the refractometer applies the correction based on sucrose which is different than wort sugars, thus there is an error in temperature correction that increases as the temperature moves from the 20° C. reference temperature.

The presently disclosed methods and apparatus provide improvements in the measurement of one or more physical properties of interest with respect to the production beer or other malt beverages. Certain embodiments are hereinafter described in detail in connection with the views and examples of FIGS. 1-7, wherein like elements refer to like elements throughout the views.

FIG. 1 illustrates the relationship between refractive index and sucrose concentration (Brix) 10, the actual concentration of dissolved wort sugars 12, and a standard refractometer correction factor of Brix 14 divided by 1.04. It is apparent that using the sucrose relationship as a measure of wort dissolved solids overstates the actual sugar concentration. Likewise, the refractometer correction factor used to help compensate for the difference between sucrose and wort sugars in brewing software and online calculators, understates the actual sugar content.

Figure 2:
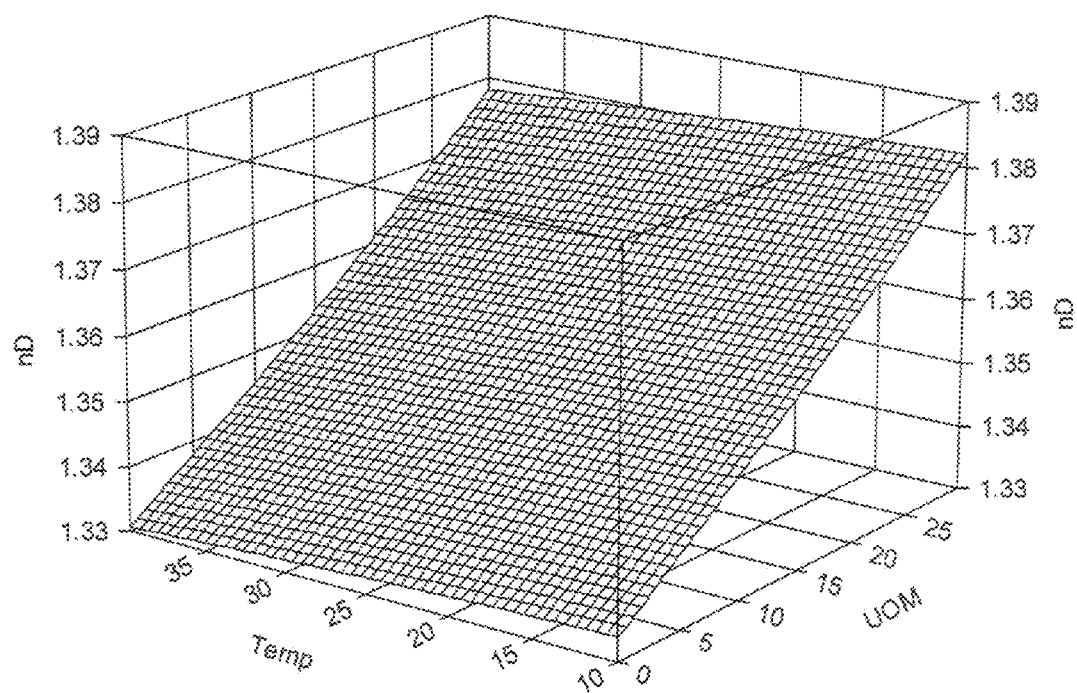
FIG. 2 shows the relationship between refractive index and wort sugar concentration at various temperatures.

It is not enough to know just the relationship between wort sugars and refractive index. When using refractive index measurements, it is necessary to also correct or compensate the refractive index value to return it to a predetermined reference temperature. Temperature correction is different for every fluid and varies nonlinearly for a fluid by both temperature and concentration. FIG. 2 represents the temperature correction specific to wort sugars. In FIG. 2, the "nD" axis represents the refractive index of wort sugars. The "Temp" axis represents the temperature of wort sugars in degrees Celsius, and the "UOM" axis represents the wort sugars or total dissolved solids. The correction for wort sugars is specific to wort sugars and is very different than the sucrose temperature correction used in existing Brix refractometers currently used for measuring beer.

The relationship between wort sugars and refractive index, together with temperature correction specific to wort, were programmed into a digital handheld refractometer, herein referred to as the "Test Unit". Twelve different wort samples were then tested on an industry-standard Anton Paar DMA5000 digital density meter (accurate to +/−0.000005 specific gravity D20/20). The Anton Paar instrument was also used to determine wort original extract (a measure of dissolved solids). Samples from the same worts were then tested on an Atago WM-7 refractometer (accurate to +/−0.1% Brix) and on a Test Unit with the wort sugar programming. FIG. 3 is a table of the results of the testing.

In FIG. 3, column 30 represents the sample ID number of each of the worts tested. Column 31 is the specific gravity measurements as made on the Anton Paar meter. Column 32 represents the measurements made on the Test Unit which was programmed to report the specific gravity of the wort samples. It is apparent from the results in Column 33 that there was excellent agreement between the Anton Paar reference and values reported by the Test Unit.

Referring still to FIG. 3, values for original extract of the wort samples, as determined on the Anton Paar meter (34) were compared with original extract values determined using a sucrose-based Brix refractometer (35) and the Test Unit with the wort sugar programming. It is apparent from the data in column 36 that there is an error that increases with wort sugar concentration. This error is due to the difference between the sucrose base measurements and the true wort sugars. As is apparent from the columns 37 and 38, the difference between the Anton Paar original extract readings 34 and original extract readings as dissolved solids on the Test Unit match much better and do not demonstrate the same systemic error.

Figure 4:
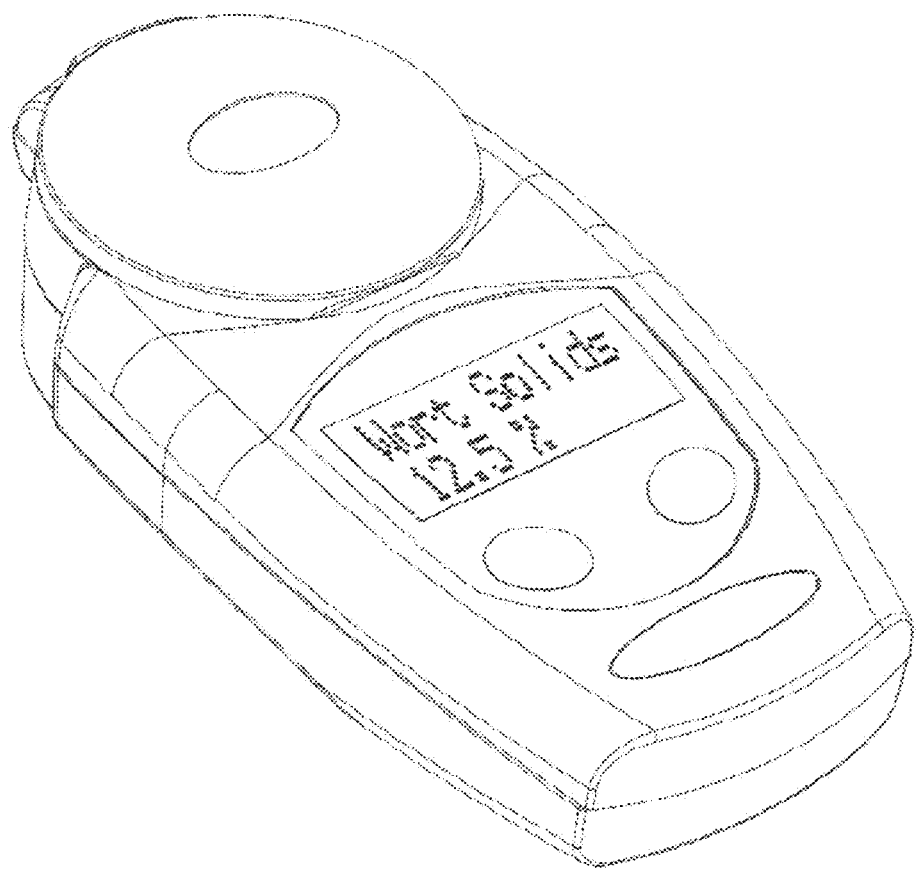
FIG. 4 depicts a digital handheld device.

The Test Unit can include an optical measurement system having a refractometer. In one embodiment, the Test Unit can comprise a handheld digital refractometer, as shown in FIG. 4. The handheld digital refractometer can include a sensing element having an optical sensor capable of determining the refractive index of a substance (e.g., a malt beverage sample) using the principle of total internal reflection. For example, with reference to FIGS. 5A and 5B, the sensing element can comprise an LED 100, a light filter assembly 102, a first optical element 104, a second optical element 106, a light sensor (e.g., a linear array of photodiodes 114), and electronic circuitry, including a temperature sensor and/or other temperature measuring circuitry. It will be appreciated that, in other embodiments, the sensing element might not be provided within a handheld digital refractometer, but might instead be provided within an inline device (FIG. 7), a tabletop or benchtop device, or otherwise.

The refractometer can also include an output device from which one or more units of measurement relating to physical properties of a fluid sample can be communicated, or output, to a user. For example, the digital display of the handheld digital refractometer of FIG. 4 can be configured to display any physical property of wort related to refractive index, such as dissolved solids, specific gravity, density, brewer's points, etc. It will also be appreciated that a handheld digital refractometer or other device might not include a digital display (e.g., such as the digital display shown in FIG. 4), but might rather communicate signals or information audibly, remotely (wired or wirelessly) to one or more other devices, or otherwise. For example, it will be appreciated that the Test Unit or other arrangement incorporating an electronic refractometer (e.g., inline, handheld, or desktop) can be connected directly to a computer via USB, Bluetooth, etc., with the user interface of the refractometer controlled on the connected device. Processing, conversion, memory, user input, display, and/or other functions can be provided on the connected device. For example, the Test Unit can include a memory storage device that can be configured to store and recall results from previous measurements. The Test Unit can also include a user input device that can be configured to receive input entered by a user and store the input in the memory storage device. In one embodiment, testing by the refractometer can be controlled automatically by a connected device, and/or incorporated into an automated system for monitoring physical properties associated with a brewing process. For example, one or more units of measurement of physical properties can be measured and compared with one or more desired predetermined values for such properties and a brewing or other process can be automatically altered based upon such measurements resulting from the refractometer and/or calculations relating thereto. Additionally, a handheld refractometer can be connected to a computer, tablet, smart-phone, etc. wirelessly and also automatically enter data into equations.

LED 100, in this example, can have a peak transmission wavelength of about 589.3 nm or be so filtered as to pass only a particular wavelength of interest. Light energy emitted from LED 100 can travel along a path forming a predetermined angle of incidence relative to a measuring surface 110. This light energy can be first conditioned by light filter assembly 102, which can comprise some combination of a light filter, light diffuser, and/or polarizer, before passing through first optical element 104. First optical element 104 can be a lens positioned directly in the path of incident light energy and so constructed as to collimate or focus this light energy. Light energy transmitted by first optical element 104 can then fall on a light incident face 108 of second optical element 106. Second optical element 106 can comprise a prism, a hemispheric element, or any of a variety of other suitable components. The second optical element 106 is shown to have the light incident face 108, the measuring surface 110 or interface which can be in physical communication with a substance of interest, and a reflected light face 112. Light energy received at the light incident face 108 can then be further directed toward measuring surface 110 of second optical element 106 at an angle relative to this surface and dependent on the refractive index of second optical element 106.

In the presence of air at the interface with measuring surface 110, all light energy can be totally internally reflected at measuring surface 110 at an angle equal to its angle of incidence. This light energy can then be directed toward and pass through reflected light face 112 of second optical element 106, and fall upon linear array 114, so positioned as to absorb all incident light energy. In this state, associated electronics scanning linear array 114 can determine that all of the photodiodes in a particular range of interest have a strong degree of light energy incident upon them.

Figure 5A:
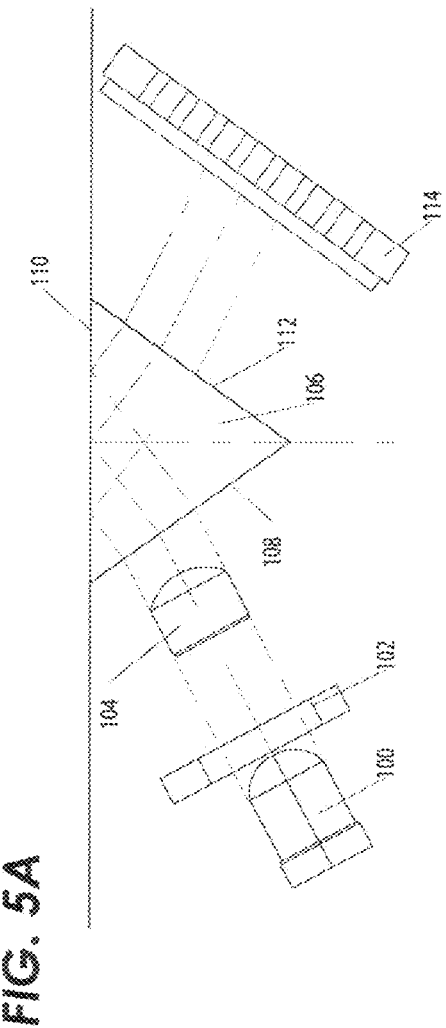
FIGS. 5A and 5B show a portion of a digital refractometer configured for measuring wort sugars, such as can be provided as part of the digital handheld device of FIG. 4.
Figure 5B:
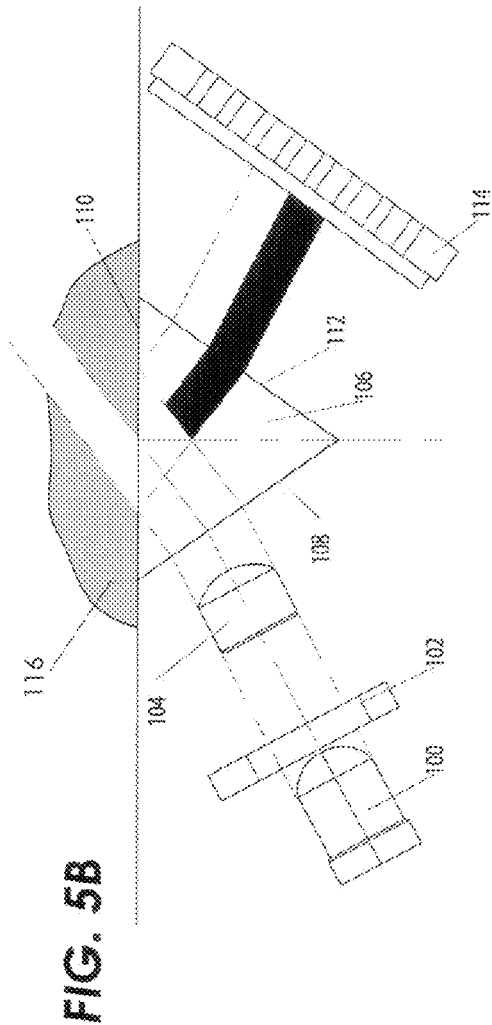

With reference to FIG. 5B, in the presence of wort 116, at the interface with measuring surface 110, a substance with a refractive index higher than that of ambient air, some of the light energy incident upon the measuring surface 110 can be transmitted into and become optically coupled with the wort 116 while some of the light energy can be directed towards and pass through reflected light face 112 of second optical element 106, and thereafter fall upon linear array 114. In this case, since some light energy was transmitted into wort 116 and lost, and still other light energy was able to be reflected onto linear array 114, the region of linear array 114 previously defined by the range of totally internally reflected light now has an illuminated region and a dark region. The boundary between this illuminated and dark region is a phenomena caused by the critical angle of the wort concentration, relative to its refractive index, and will move up and down the face of linear array 114 depending upon changes in concentration or temperature of the wort 116. A temperature sensor, for example, can adequately compensate for changes in the refractive index of a substance under test using predefined temperature corrections specific to wort 116 concentrations and temperature. Once the temperature-compensated measured refractive index is determined, a processor, which can receive signals from both the light sensor and the temperature sensor (e.g., a first signal relating to a refractive index measurement and a second signal for conversion into usable units of temperature), can convert the temperature-compensated measured refractive index into a value corresponding to one or more physical properties of wort such as specific gravity, density, dissolved solids, brewer's points, etc.

In one embodiment, the processing unit can convert signals from the linear array 114 directly into unit of measure readings, thereby bypassing the use of refractive index entirely, though the underlying method of measurement would still be by-and-large index of refraction, regardless of the units used.

Figure 6:
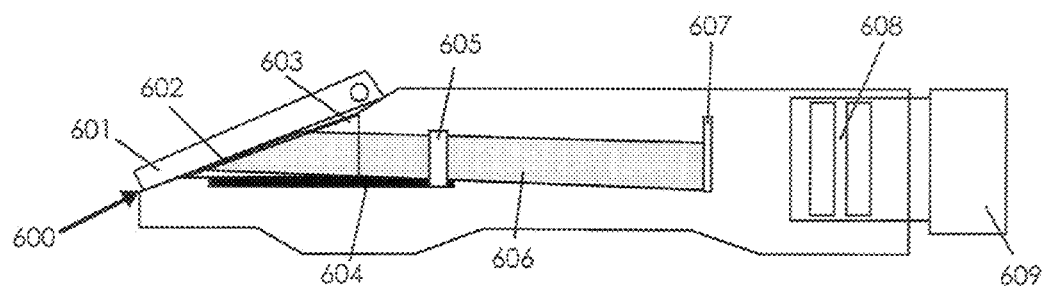
FIG. 6 shows a portion of an analog refractometer for measuring wort sugars.
Figure 7:
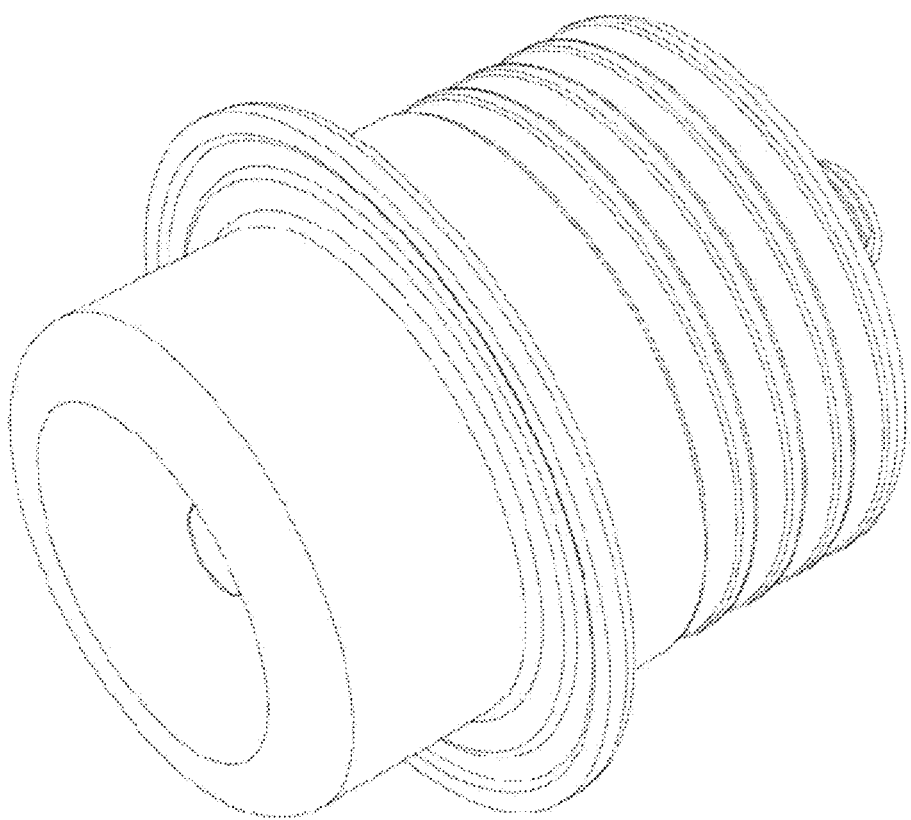
FIG. 7 depicts an inline device comprising the portion of the digital refractometer of FIG. 5, wherein the inline device is shown to include a sanitary tri-clamp fitting such as for use in the food and beverage industry.

In accordance with another embodiment, the apparatus in FIG. 6 can comprise an optical measurement system. The optical measurement system can comprise a sample cover 601, a first optical element 603 in the form of a prism, with a measuring surface 602, a second optical element 605, a reticle 607, a temperature compensating arrangement 604, and magnifying device 608. The apparatus in FIG. 6 can be configured so that light energy incident at a grazing angle 600 to measuring surface 602 is transmitted through a wort sample and through measuring surface 602. Optical energy 606 can then be transmitted through optical element 603 whereupon a shadowline caused by the critical angle of refraction of the wort sample can then be focused by optical element 605 onto reticle 607. A predetermined scale specific to wort sugars can be etched or otherwise inscribed onto a surface of the reticle and the position of the shadowline relative to the scale's divisions can be directly related to one or more physical properties of the wort under test. A magnifying means 608 can enlarge the scale image and shadowline impinging on the reticle 607 and can make the reticle 607 image human readable through eyepiece 609.

Although the problem of measuring wort on a sucrose-based Brix refractometer has existed for more than a hundred years, and although others have tried to solve the problem by using external software or calculations to estimate the difference, until now there has not been a definitive method or apparatus capable of providing the correct properties of wort sugars relative to refractive index. Furthermore, sucrose-based temperature correction or compensation simply is not adequate for measuring the complex sugar profile associated with wort and wort-based temperature correction. The present methods and apparatus can take into account the behavior of wort relative to refractive index, and can calculate a correction model sufficient to temperature correct the refractive index readings relative to wort sugars.

While some may consider a malt beverage to be the fermented wort, wort as used herein refers not to the beverage itself, but rather to an ingredient or precursor for a beverage. A malt beverage sample, as discussed herein, can include an ingredient or a precursor, such as wort, for a beverage. Also, a malt beverage sample, as discussed herein, can include a beverage itself, such as beer, either during its process of formation or in its completed form. The present methods and apparatus are useful for measuring one or more physical properties of wort. However, the present methods and apparatus can also be used to measure beer during or after fermentation, provided the user has the original dissolved solids reading before fermentation and performs a manual calculation or has access to a brewing calculator or brewing software. Or, during or after fermentation, the user can take a dissolved solids reading and a specific gravity reading with a hydrometer and input those values into brewing software or a calculator.

In one embodiment, it will be appreciated that certain methods and apparatus herein, such as the disclosed relationship between wort sugars and refractive index, including temperature correction, can be provided as part of brewing software, an application, an online calculator, or otherwise, apart from or perhaps not even associated with a refractometer. In another embodiment, it will be appreciated that wort temperature correction could be applied to the relationship between sucrose and refractive index, should the Brix unit of measure be desirable to a user.

The foregoing description of embodiments and examples has been presented for purposes of illustration and description. It is not intended to be exhaustive or limiting to the forms described. Numerous modifications are possible in light of the above teachings. Some of those modifications have been discussed, and others will be understood by those skilled in the art. The embodiments were chosen and described in order to best illustrate principles of various embodiments as are suited to particular uses contemplated. The scope is, of course, not limited to the examples set forth herein, but can be employed in any number of applications and equivalent devices by those of ordinary skill in the art.

What is claimed is:

1. A method for determining a physical property of a malt beverage sample, the method comprising:
   measuring a refractive index of the malt beverage sample;
   determining a temperature-compensated measured refractive index by temperature correcting the measured refractive index relative to a predetermined reference temperature, wherein the temperature correcting is specific to the total dissolved solids, rather than simply the sucrose content, of the malt beverage sample; and
   converting the temperature-compensated measured refractive index to a unit of measurement, wherein the unit of measurement relates to a physical property of the malt beverage sample.

2. The method of claim 1, further comprising measuring a temperature of the malt beverage sample, wherein the temperature correcting occurs in response to the measured temperature.

3. The method of claim 2, wherein:
   the malt beverage sample comprises wort; and
   the physical property is selected from the group consisting of total dissolved solids, specific gravity, density, and brewer's points.

4. The method of claim 3, further comprising outputting the unit of measurement.

5. The method of claim 4, wherein the outputting the unit of measurement comprises displaying the unit of measurement on a digital display.

6. The method of claim 5, wherein each of the measuring the refractive index, the measuring the temperature, the determining the temperature-compensated measured refractive index, the converting, and the displaying is accomplished by a handheld device.

7. The method of claim 6, wherein:
   the malt beverage sample comprises wort; and
   the unit of measurement displayed on the digital display is total dissolved solids of the wort.

8. The method of claim 4, wherein the outputting the unit of measurement comprises communicating the unit of measurement to a remote device.

9. The method of claim 1, further comprising:
   comparing the unit of measurement to a desired predetermined value; and
   issuing instructions to alter a brewing process according to results of the comparing.

10. The method of claim 1, wherein the measuring the refractive index is accomplished by an inline device.

11. The method of claim 1, wherein:
    the measuring the refractive index is accomplished by a refractive index sensor of a handheld device; and
    the refractive index sensor comprises:
      a light source;
      a prism comprising a light incident face, a measurement surface, and a reflected light face, the prism is configured to permit at least a portion of the emitted light energy to pass through the light incident face, become incident upon the measurement surface, and reflect therefrom through the reflected light face; and
      a light sensor configured to receive and measure light energy from the reflected light face of the prism.

12. The method of claim 1, wherein:
    the measuring the refractive index is accomplished by a handheld device;
    the handheld device comprises a reticle having a scale;
    the scale is configured to register a shadowline resulting from a critical angle of refraction of the malt beverage sample, such that a position of the shadowline relative to the scale corresponds to the unit of measurement; and
    the handheld device further comprises a magnifying device which enlarges the scale and shadowline on the reticle to facilitate human readability of the unit of measurement.

13. An apparatus configured for determining a physical property of a malt beverage sample, the apparatus comprising:
    a refractive index sensor;
    a temperature sensor; and
    a processor configured to receive a first signal from the refractive index sensor and a second signal from the temperature sensor, wherein the processor is configured to:
      convert the first signal to a refractive index measurement;
      determine a correction factor in response to the second signal, wherein the correction factor is specific to the total dissolved solids, rather than simply the sucrose content, of a malt beverage sample;
      apply the correction factor to the refractive index measurement to obtain a temperature-compensated refractive index measurement; and
      convert the temperature-compensated refractive index measurement into a unit of measurement relating to a physical property of a malt beverage sample.

14. The apparatus of claim 13, wherein the physical property is selected from the group consisting of total dissolved solids, specific gravity, density, and brewer's points.

15. The apparatus of claim 14, further comprising an output device, the output device being configured to communicate the unit of measurement to a user.

16. The apparatus of claim 15, wherein the output device comprises a digital display configured to display the unit of measurement.

17. The apparatus of claim 16, wherein the unit of measurement displayed on the digital display is total dissolved solids of wort.

18. The apparatus of claim 17 being a handheld device.

19. The apparatus of claim 18 wherein the refractive index sensor comprises:
    a light source configured to emit light energy;

a prism comprising a light incident face, a measurement surface, and a reflected light face, the prism is configured to permit at least a portion of the emitted light energy to pass through the light incident face, become incident upon the measurement surface, and reflect therefrom through the reflected light face; and a light sensor configured to receive and measure light energy from the reflected light face of the prism.

20. The apparatus of claim 13, further comprising:

a memory storage device configured to store and recall results from previous measurements; and a user input device configured to receive input from a user and store the input in the memory storage device.

\* \* \* \* \*